Figure 1:
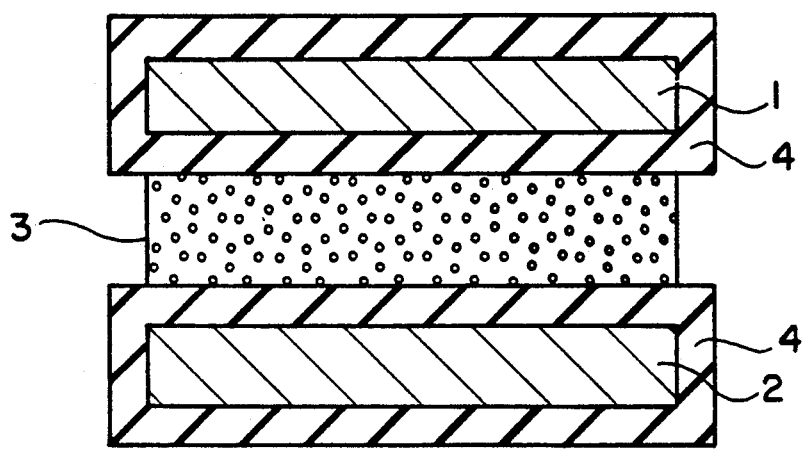

United States Patent

Chmiel et al.

[11] Patent Number: 5,269,175
[45] Date of Patent: Dec. 14, 1993

[54] SENSOR FOR INVESTIGATING LIQUIDS

[75] Inventors: Horst Chmiel, Leonberg; Günter Hellwig; Herbert Bauser, both of Stuttgart, all of Fed. Rep. of Germany

[73] Assignee: Fraunhofer-Gesellschaft zur Forderung der angewandten Forschung e.V., Munich, Fed. Rep. of Germany

[21] Appl. No.: 737,924

[22] Filed: Jul. 29, 1991

Related U.S. Application Data

[63] Continuation of Ser. No. 617,420, Nov. 20, 1990, abandoned, which is a continuation of Ser. No. 492,283, Feb. 28, 1990, abandoned, which is a continuation of Ser. No. 346,377, Apr. 28, 1989, abandoned, which is a continuation of Ser. No. 201,389, May 27, 1988, abandoned, which is a continuation of Ser. No. 65,622, Jun. 23, 1987, abandoned, which is a continuation of Ser. No. 804,655, Jan. 21, 1986, abandoned.

[30] Foreign Application Priority Data

Apr. 6, 1984 [DE] Fed. Rep. of Germany ....... 3413135

[51] Int. Cl.[5] .............................................. G01N 33/30
[52] U.S. Cl. ................................... 73/53.05; 324/675
[58] Field of Search ............ 73/53, 61 R, 61.1 R, 73/64, 73, 335, 336.5, 53.05; 324/675, 674, 678, 679, 667, 668, 659, 669, 670

[56] References Cited

U.S. PATENT DOCUMENTS

| | | | |
|---|---|---|---|
| 2,681,571 | 6/1954 | Becker | 73/336.5 |
| 2,976,728 | 3/1961 | Brogan et al. | 73/61.1 R |
| 3,192,426 | 6/1965 | Feuer | 73/336.5 |
| 3,269,180 | 8/1966 | Schreiber | 73/61 R |
| 3,437,924 | 4/1969 | Tocanne | 324/61 P |
| 3,453,143 | 7/1969 | Reynolds et al. | |
| 3,746,974 | 7/1973 | Stoakes et al. | 324/61 P |
| 3,959,764 | 5/1976 | Allman | 73/27 R |
| 4,260,950 | 4/1981 | Hadden et al. | 73/1 R |
| 4,352,059 | 9/1982 | Suh et al. | 324/61 R |
| 4,482,882 | 11/1984 | Luder et al. | 73/336.5 |
| 4,561,293 | 12/1985 | Richards | 73/73 |
| 4,571,543 | 2/1986 | Reymond et al. | 324/425 |
| 4,757,252 | 7/1988 | Maltby et al. | |

FOREIGN PATENT DOCUMENTS 58102  8/1982 European Pat. Off. .
2938434 11/1979 Fed. Rep. of Germany .

Primary Examiner—Jerry W. Myracle
Attorney, Agent, or Firm—Kalish & Gilster

[57] ABSTRACT

The invention relates to a sensor with two electrodes and a non-conducting diaphragm arranged between them. The electrodes have an insulating coating, which preferably comprises a metal oxide, mixed metal oxide, metal nitride, inorganic insulating material or fluorocarbon and the non-conducting diaphragm a metal oxide, mixed metal oxide, inorganic or organic insulating materials. As a function of the intended use, the diaphragm and electrode coating are porous (for measurements in non-aqueous liquids) or non-porous (for measurements of aqueous liquids). It is also directed at a process for measuring the characteristics of a liquid with the sensor according to the invention, as well as to the use of the sensor for the continuous or discontinuous investigation of liquids.

25 Claims, 4 Drawing Sheets

SENSOR FOR INVESTIGATING LIQUIDS

This application is a continuation of application Ser. No. 07/617,420, filed Nov. 20, 1990, now abandoned which is a continuation of 07/492,283, filed Feb. 28, 1990, now abandoned, which is a continuation of 07/346,377, filed Apr. 28, 1989, now abandoned, which is a continuation of 07/201,389, filed May 27, 1988, now abandoned, which is a continuation of 07/065,622, filed Jun. 23, 1987, now abandoned, which is a continuation of 06/804,655, filed Jan. 21, 1986, now abandoned.

TECHNICAL FIELD

The invention relates to a sensor for testing, investigating or examining liquids and an apparatus for measuring the characteristics of a liquid by means of said sensor.

In the past attempts have been made in the most varied ways to produce sensors for the continuous and discontinuous investigation of the characteristics of liquids. Thus, for example, conventionally sensors are used for determining pH-value fluctuations in reactors or physiological pH-values in blood samples and the like. Compared with optical processes, e.g. spectroscopic processes, which can also be used continuously or discontinuously, sensors have the advantage that they are independent of turbidity or impurities influencing the light transmission and can be directly used in samples.

PRIOR ART

Sensors for detecting quantitative changes to liquids are known from DE-OS 21 55 568. The latter discloses a sensor constructed as a capacitor, in which a plastic foil made from a material swelling in water is used as the capacitor dielectric and the capacitance is a measure for the concentration of water or components dissolve therein. The sensor known from DE-OS 21 55 568 suffers from the disadvantage that water-swelling plastic membranes or diaphragms have different physical characteristics as a function of their storage or age, so that it is frequently necessary to recalibrate such sensors. The water-swellable plastics are also unusable or difficultly usable in corrosive media or in mixtures of water and organic solvents.

German patent 925 621 discloses a sensor of a different type, in which a capacitor with insulated electrodes is used for determining the dielectric constant of a gaseous medium introduced between the capacitor electrodes. In addition, the capacitance of the capacitor is measured as a function of the medium introduced. This probe makes it possible to determine the dew point of the gaseous medium to be investigated.

"Technisches Messen tm, 1979, No. 255-259" discloses a process for determining the complex dielectric constant of liquids with very high energy absorption in the decimetric wave band, the sample to be investigated being enclosed in a coaxial resonator and the resonant frequency shift and quality change of the resonance system is determined under the influence of the material to be investigated in the resonator.

The coaxial resonator described therein requires the introduction of liquid into the resonator cavity, so that only a discontinuous measurement and not a continuous measurement is possible. The construction of such a resonator also requires considerable technical effort and expenditure, even for sealing purposes alone, so that it is not a robust, widely usable probe, which can be employed for continuous operation, e.g. in bioreactors, for measuring engine oils in use and the like.

DESCRIPTION OF THE INVENTION

The problem of the present invention is therefore to provide a sensor, which has a simple, robust construction and which is usable for discontinuous and/or continuous measurement operation in liquids.

It is a further object of the invention to provide a sensor, whose dimensions are so small that, without difficulty, it can be used in the smallest liquid volumes.

In addition, the sensor according to the invention is intended to be suitable for detecting different liquid characteristics, i.e. it is to be universally usable.

In addition, an apparatus is to be provided which, in conjunction with the sensor according to the invention, permits a quantitative measurement of liquid characteristics.

An inventive solution of this problem and the other objects referred to is characterized by further developments thereof in the claims.

According to the invention the electrodes have an electrically insulating coating which is liquid-tight. The liquid to be investigated can merely penetrate the membrane or diaphragm and in fact "diffuses into" e.g. the pores or directly into the diaphragm material. The complex resistance of the capacitor formed by the electrodes and between which there is a dielectric formed by the coating of one electrode, the diaphragm and the coating of the other electrode is consequently only changed by the liquid in the diaphragm, but not e.g. by ohmic components of a through direct connection, such as would e.g. result from a liquid filament between the electrodes.

As the diaphragm is also made from a material which is not chemically attacked by the liquid to be investigated, there is a high reproducibility of measurements with the sensor according to the invention, so that the change to the complex relative permittivity of the diaphragm when liquid penetrates the same or the complex capacitance of the capacitor formed by the electrodes can be very accurately used for investigating changes to the characteristics of liquids.

It is particularly advantageous if the electrodes are essentially made from a metal and/or transition metal and particularly from aluminium, zirconium, titanium, tantalum, tungsten or molybdenum, particular preference being given to the production of the electrodes from pure titanium or a titanium alloy, e.g. with a content of up to 6% aluminium and up to 4% vanadium and optionally copper according to claim 8.

The non-conducting diaphragm, which absorbs or is in contact with the medium to be investigated comprises, in preferred manner aluminium oxide, silicon nitride, $[KAl_2(OH)_2]*[AlSi_3O_{10}]$, titanium oxide or polytetrafluoroethylene.

Advantageous materials for the electrode coatings comprise a non-conducting metal oxide, mixed metal oxide, metal nitride, an inorganic insulating material or fluorocarbon, particular preference being given to oxides, $Al_2O_3$ or titanium oxide or mixed oxides, such as titanium-aluminium zirconate. The coatings can be produced by direct oxidation of the electrode material, e.g. by anodic or glow oxidation in per se known manner as zirconium oxide, titanium oxide, tantalum oxide, tungsten oxide, molybdenum oxide or aluminium oxide on the electrodes. The electrode coatings and diaphragm can essentially be made from the same basic materials, optionally with different structures, so that it is possible to obtain the inventive characteristics of the coating (liquid-tight) and diaphragm (not liquid-tight).

According to a particularly preferred embodiment of the sensor according to the invention, which is particularly suitable for the measurement of oils, the non-conducting diaphragm is porous with through pores, whose diameter ranges approximately between 0.01 and 1 $\mu$m and preferably between 0.05 and 0.2 $\mu$m. Surface charges form in the pores between the oil inclusions and the insulator comprising the membrane. These surface charges not only influence the dielectric constance of the capacitor as a function e.g. of the alkalinity of the oil, as well as the dispersant/detergent/additive concentration but the mobility of the surface charges detected via dynamic measurements also constitutes a measure for the viscosity of the oil, so that surprisingly the sensor according to the invention also makes it possible to very accurately measure the viscosity. Thus, the sensor according to the invention is ideally suited to the measurement of the characteristics of in particular industrial oils, as will be explained in greater detail hereinafter.

The diaphragm material can also not have pores in the aforementioned sense and is instead liquid-tight, but a pore function is achieved through gaps, cavities, etc, which are obtained during the (fixed) superimposing of layers of diaphragm material or the superimposing of the two insulated electrodes. In certain circumstances there is no need for the diaphragm in the above sense, because the gap between the coatings serves as the diaphragm.

However, as a function of the measuring problem, it can be advantageous for the "specific pore surface" to be as large as possible, e.g. approximately 100 m$^2$/g not only when measuring in oils, but also when measuring ion activities and particularly pH-value, if the liquid or ions are not to diffuse into the diaphragm.

At least one of the electrodes can be porous and the inner walls of the porous electrode have a non-conducting coating, which is substantially liquid-tight. It is also possible in this embodiment to obviate the diaphragm and e.g. to only place the two insulated electrodes upon one another. When using a diaphragm, its thickness can be between 10 and 100 $\mu$m and preferably between 20 and 40 $\mu$m.

In a further preferred embodiment of the sensor according to the invention, which is particularly suitable for use in water, aqueous solutions or hydrous liquids, the diaphragm is not porous and instead comprises a material into which can diffuse oil or hydrogen and/or hydroxyl ions or other ions, so that e.g. a pH-value change leads to a dielectrically behaving diaphragm material. It is particularly preferred for the diaphragm to comprise non-porous corundum, aluminium hydroxyl silicate, such as e.g. mica, or gamma-alumina, i.e. materials with a layer lattice structure, in which inclusions can rapidly penetrate between the individual layer lattices. The diaphragm thickness in this preferred embodiment is between approximately 6 and 100 $\mu$m, preferably 30 to 40 $\mu$m.

The sensor suitable for measurement in aqueous solutions is at least partly enclosed by an ion-selective diaphragm, which e.g. increases the selectivity for hydrogen or hydroxyl ions, potassium, sodium, chloride, calcium or magnesium ions, so that it is possible to determine these ions.

The electrodes can be arranged in the manner of a plate capacitor, but it is also possible to have one electrode cylindrically surround the other electrode, as in the case of a cylindrical capacitor.

In the case of an inventive apparatus for measuring the characteristics of a liquid, the sensor is introduced into the liquid, a variable a.c. voltage between 50 Hz and 1 GHz is applied to the electrodes and the dielectric loss factor D and/or capacitance C is determined as a function of the measurement frequency. The measured values obtained in this way are stored in an evaluation unit which, on the basis of corresponding pairs of dielectric loss factor/frequency measured values or the dependence of the capacitance on the frequency is able on the basis of a comparison with reference value stored in the evaluation unit to determine the characteristics of the liquid, such as the viscosity, pH-value, ion content and the like.

As has already been stated, a particularly preferred possible use consists of the monitoring of oils or the like, such as e.g. motor, engine, turbine, pump, transformer and similar. As a result of the use of sensor according to the invention, it is possible to constantly investigate the characteristics of an oil in use, it being optionally possible by means of the stored measured values to add in a controlled manner additives to the oil being used, so that the characteristics thereof are positively influenced.

Oils must at least be replaced when their functionality has dropped to a just acceptable value. Hitherto the oil has been replaced without further checking of its actual ageing on the basis of a determined average "maintenance period". In the case of an excessively early oil change this leads to increased oil costs, or in the case of an excessively late oil change to increased wear to engine parts.

Important characteristics of engine lubricating oils are the lubricating action (friction reduction), corrosion protection and the protection of running parts against the action or deposition of particulate impurities.

These oil characteristics can be obtained in that additives are added for improving the viscosity and to ensure an adequate lubricating action. The oil is adjusted to an alkaline pH to prevent chemical corrosion. Contaminating particles are held in finely divided form in the oil by detergents and/or dispersants, so that no deposition or collection of such particles takes place.

When an oil is in use, oxidative degradation (acid group formation) reduces the alkalinity. The viscosity either increases or decreases as a function of the operating conditions. Thus, the testing of the functionality of the oil, such as is e.g. desired in the case of engines with varying loading, e.g. those used in heavy land vehicles should therefore extend to the three main properties alkalinity, viscosity and dispersant/detergent additive concentration.

It is known to determine the qualitative characteristics of oil in the laboratory by means of samples, e.g. using polarography viscosimetry. The oil pressure can also be constantly measured and this provides indirect information on the viscosity of the oil. It is finally possible to constantly measure the conductivity of the oil, which provides an overall information picture on ionic impurities in the oil. However, these known methods are too complicated and costly for a continuous testing of the oil during the operation of the engine, e.g. in a moving vehicle, because they either require the taking of samples, i.e. cannot be performed in a closed engine oil circuit, or because they require different very large measuring means.

The probe according to the invention makes it possible for the first time to continuously monitor the oil characteristics in an advantageous manner. It is surprisingly possible to construct such probes in such a way that, despite small dimensions, they provide satisfactory measurements of the viscosity and alkalinity. The invention is based on the fact that the dielectric values of oils are frequency-dependent. The porous, non-conduction between the capacitor electrodes has the effect that the dielctric values display maxima or steps at different frequencies which are typical oil or oil property. Without the inventive non-conducting porous coating between the electrodes for absorbing the oil to be measured, the frequency-dependent course of the dielectric values is monotonic, i.e. no oil-specific maximum is provided.

According to the invention the capacitance, relative permittivity and dielectric loss factor can be measured and evaluated by means of a computer. The embodiment referred to hereinafter relates to the processing of the dielectric loss factor. Obviously valuable information can be obtained from the other dielectric values.

Frequency-dependent maxima of the dielectric loss factor on applying an a.c. voltage with frequencies between 50 Hz and 1 GHz are probably due to the fact that the oil-filled pores of the diaphragm, at the operating temperature of approximately 150° C., represent electrically conductive inhomogeneities in the non-conducting diaphragm, which lead to dielectric relaxation behavior, known as the Maxwell-Wagner effect. Electrically conductive particles, which are embedded in an insulator, reveal a periodic polarization when an electric a.c. field is applied with increasing frequency; an increasing amount of energy is consumed for polarizing the particles. On exceeding the relaxation frequency ($f_r$) the charge carrier amplitude becomes smaller. Therefore a maximum of the dielectric loss at the relaxation frequency and a step in the relative permittivity are obtained. Thus, oil represents poor electrically conducting inhomogeneities in the non-conducting diaphragm material and consequently exhibits the Maxwell-Wagner effect.

The charge carrier concentration in the oil is dependent on acid, alkaline and salt-like groups or degradation products of the oil, as well as the water content. On increasing the frequency, all these groups acting as charge carriers participate in the forced periodic movement but, as a result of their inherent inertia, they drop out with rising frequency. At a relaxation frequency characteristic of each charge carrier location, this takes place with a more or less marked maximum in the dielectric loss factor D or a stage in the relative permittivity or capacitance.

In the case of free oil, which is not enclosed in a diaphragm, these relaxation frequencies are below 50 Hz and cannot easily be resolved. In addition, the losses in free oil are too large to permit an adequately large measuring effect to be observed. As a result of their pores, the diaphragms according to the invention lead to a space charge layer being formed as a result of physical absorption of oil components on the diaphragm material. As a result of this space charge layer, there is a significant increase in the electrical conductivity of the oil, e.g. by a factor of 10. Thus, there is also a shift of the relaxation frequencies proportional to the conductivity towards higher values, i.e. into a more favourable frequency range from the measurement standpoints.

The probe or sensor according to the invention can now either be used in the flow-through process (particularly as a cylindrical capacitor) or in the immersion process.

When using the sensor according to the invention for pH-measurement purposes and/or for measuring the ion activity in a water-containing liquid, it can also be advantageous to make the diaphragm non-porous, but able to absorb hydrogen, hydroxyl and/or other ions.

Due to the fact that the hydroxyl and/or hydrogen ions or other ions diffuse into the diaphragm, there is a change to the dielectric behavior of the capacitor.

The pH-sensor according to the invention, which essentially only reacts to $OH^-$ and $H^+$, is particularly advantageous because, unlike in the case of the hitherto conventional glass-pH-probes, it is not fragile and can also operate at extreme pH-values, particularly in the alkaline range. It is not possible to use glass electrodes in strong alkaline solutions. Another disadvantage of the known pH-sensors is, apart from their sensitivity, that they are relatively large and can consequently not be used for very small measuring volumes.

As a result of the construction according to the invention and particularly due to the fact that a strong diaphragm is inserted between coated electrodes, it is possible to e.g. monitor the pH-value or other ion activities in electroplating baths, electrolytic baths, bioreactors, etc. In particular, a continuous measurement is possible, even at extreme alkaline pH-values.

The sensor according to the invention can also be set up for measuring other ions, e.g. potassium, sodium, chlorine, calcium or magnesium ions, in that a 15 to 20 $\mu m$ thick capsule of ion-selective diaphragm is formed round the electrodes, diaphragm and electrode coatings and this selectively permits the passage of the ions to be measured. The prerequisite for the measurement of such ions is they can penetrate or diffuse into the diaphragm material.

SHORT DESCRIPTION OF THE DRAWINGS

The invention is described in greater detail hereinafter relative to non-limitative embodiments and the attached drawings, wherein show:

FIG. 1. A cross-section through a sensor according to the invention for explaining the basic construction.

Figure 2:
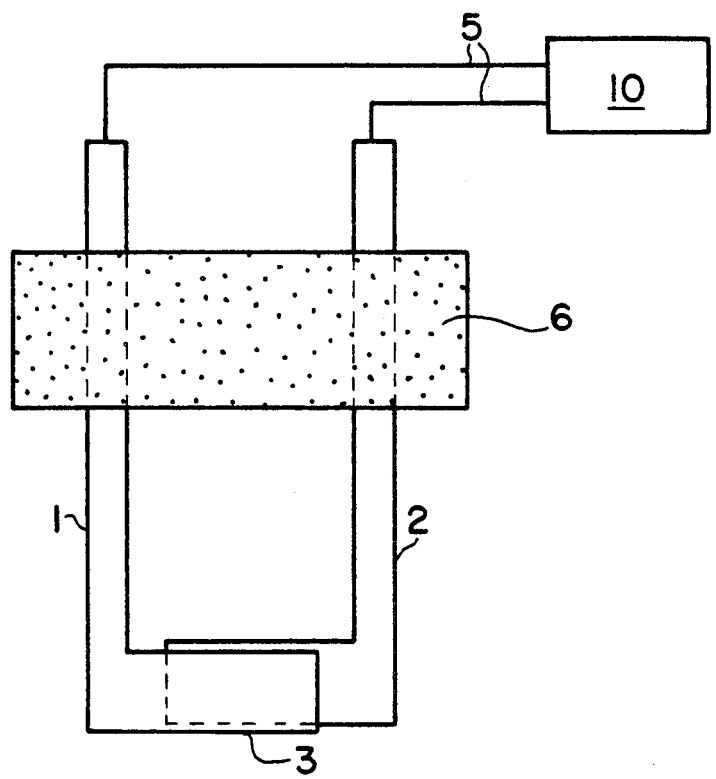

FIG. 2. A view of a possible embodiment of a sensor according to the invention.

Figure 3:
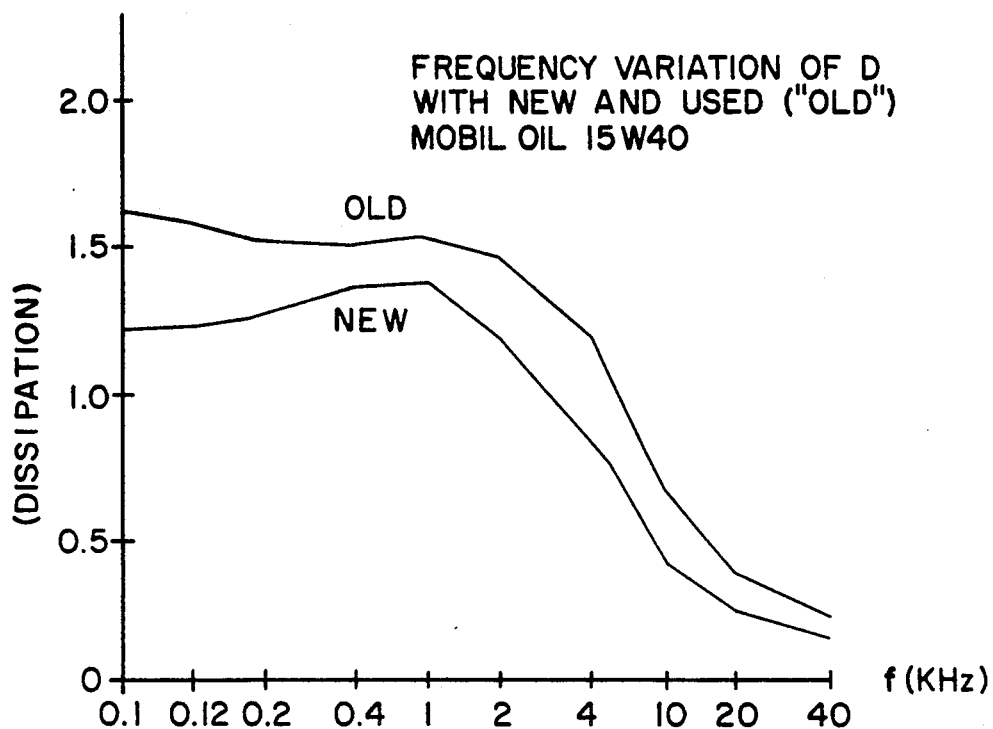

FIG. 3. A measured curve D(f) for fresh and used oil obtained with the sensor according to the invention.

Figure 4:
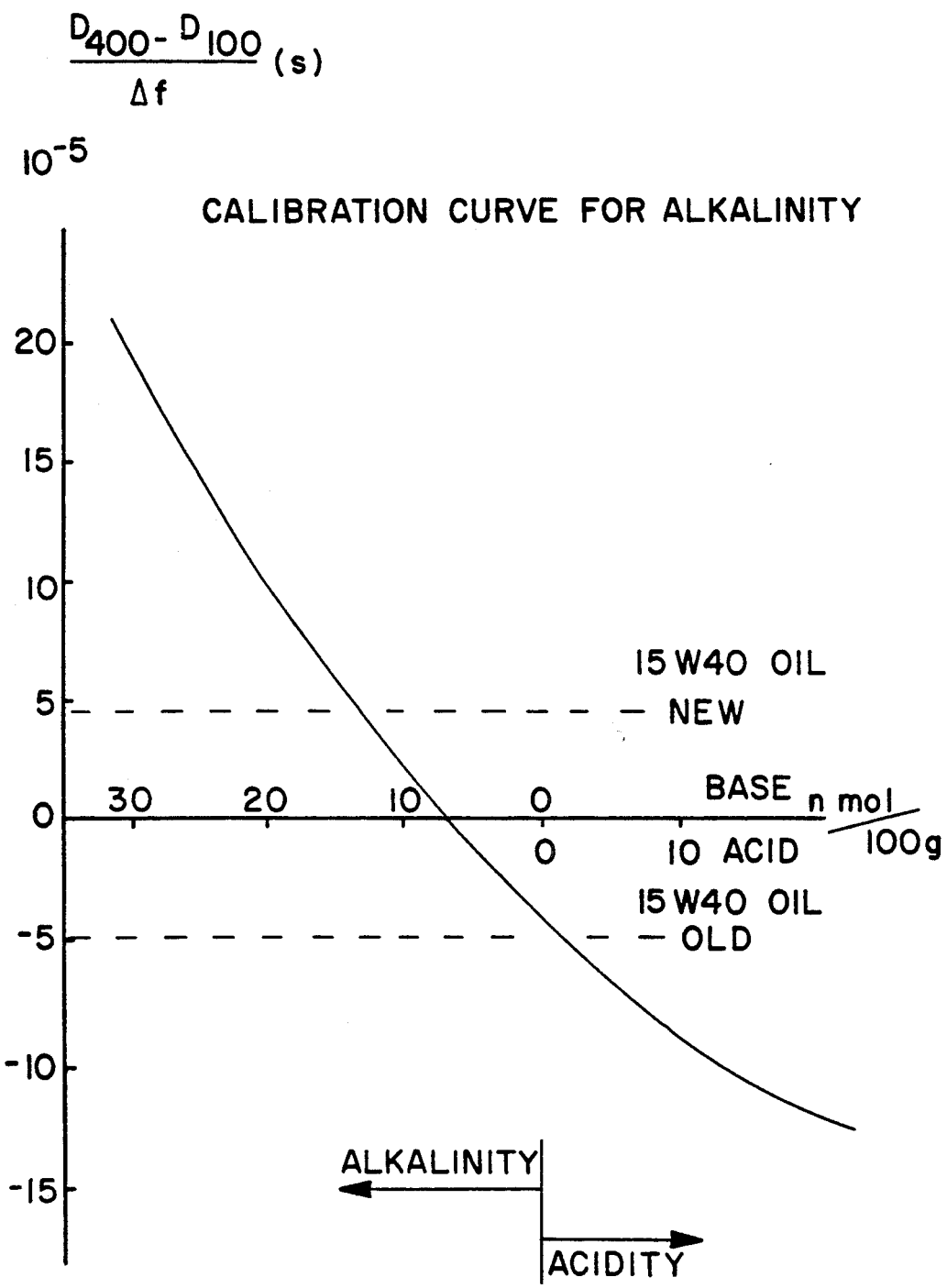

FIG. 4. A measured curve for determining the alkalinity.

Figure 5:
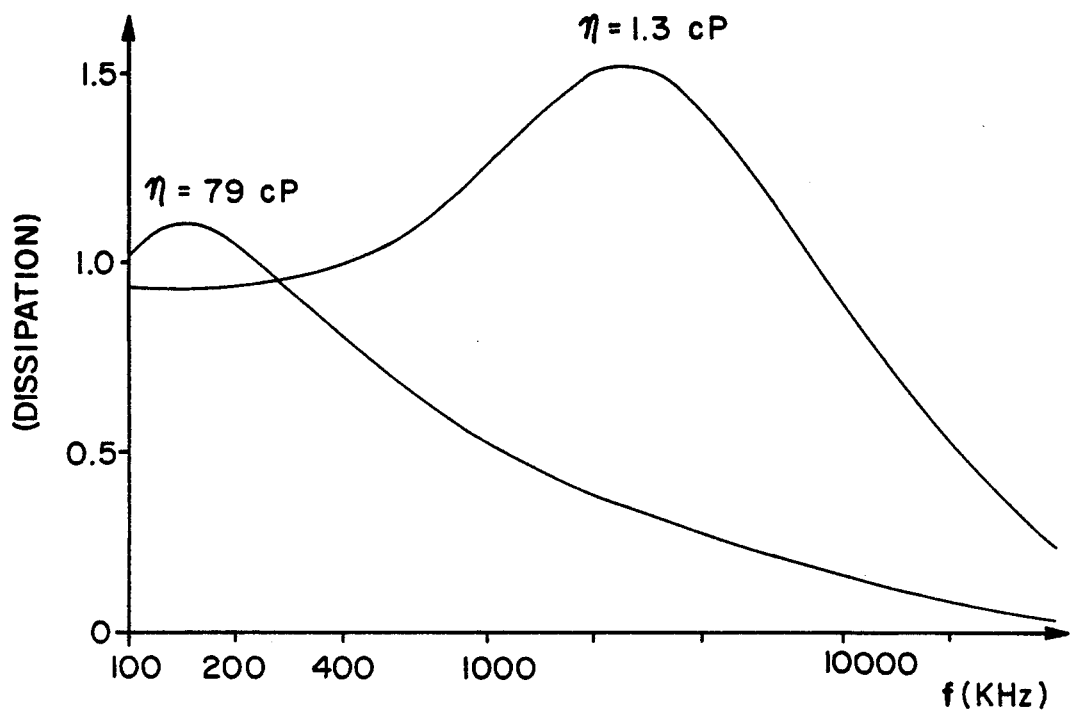

FIG. 5. The displacement of the frequency of the dielectric loss maxima as a function of the viscosity in the case of different materials.

Figure 6:
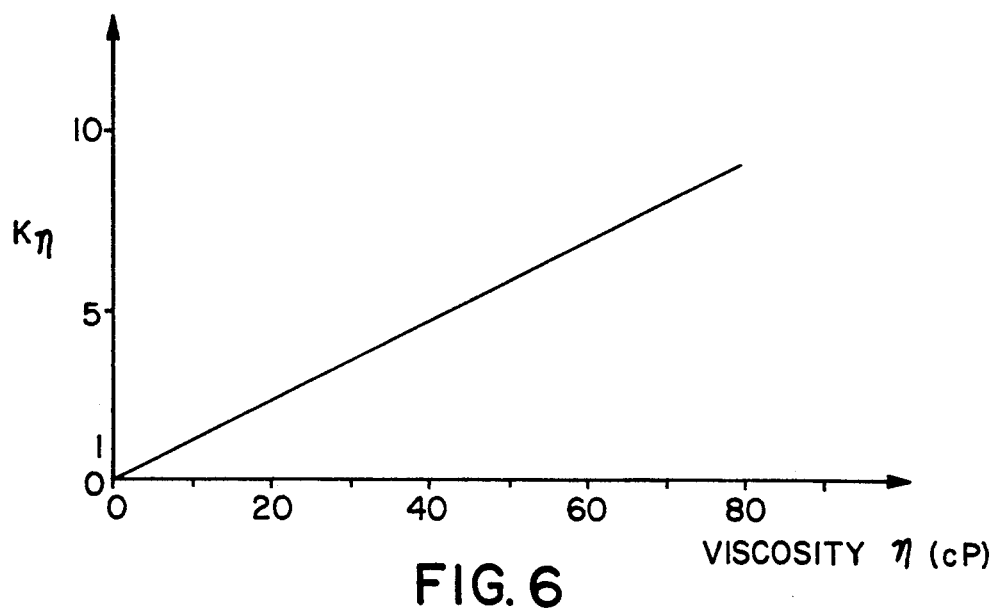

FIG. 6. The dependence of $k_n$ on $n$.

Figure 7:
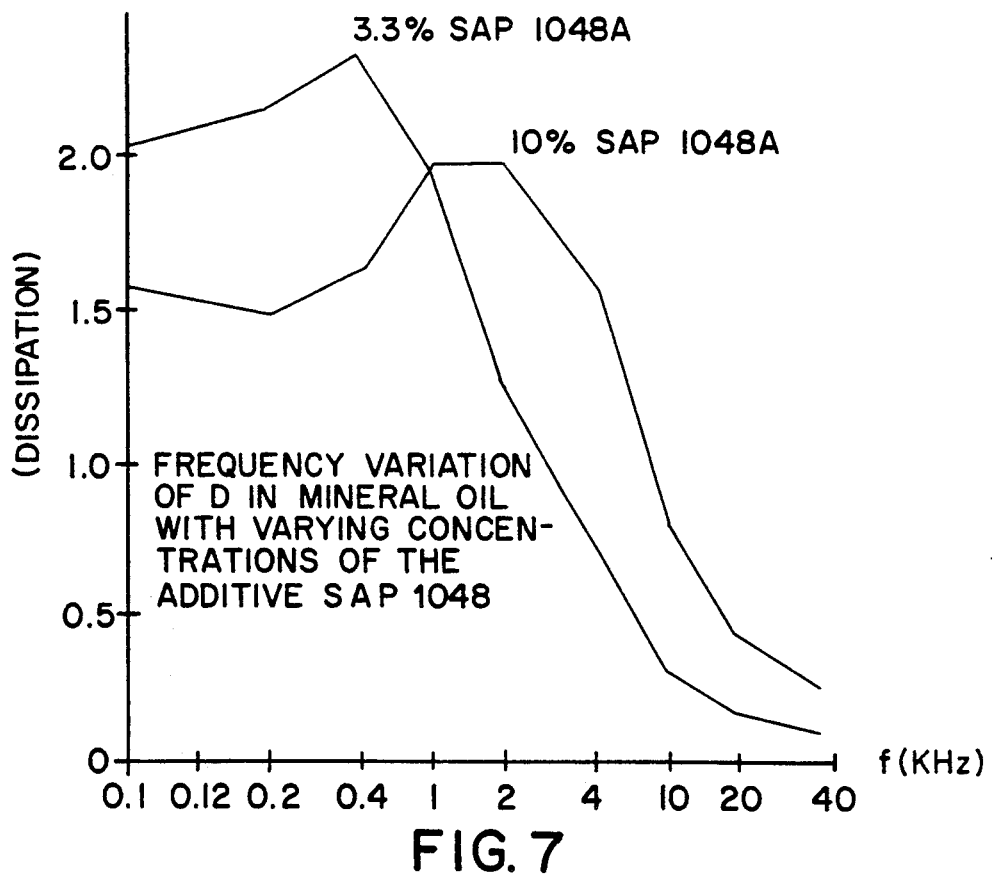

FIG. 7. The change to D on adding additives to engine oil.

WAYS TO PERFORM THE INVENTION

FIG. 1 shows, not to scale and diagrammatically, the construction of a sensor which, according to the invention, is constructed as a plate capacitor. The sensor has two electrodes 1 and 2, on which is located an electrically insulating coating 4 and between which is arranged a diaphragm or membrane 3.

A signal processing and evaluation unit is connected to the two sensor electrodes 1, 2 and applies an a.c. voltage of variable frequency to the electrodes. On the basis of the complex resistance behavior of the sensor, the evaluation unit determines the capacitance and/or dielectric loss factor of the capacitor. As will be shown hereinafter, these quantities can be used for determining the liquid characteristics to be measured with a high degree of accuracy and reproducibility, as a result of the construction of the sensor according to the invention.

As the construction of the signal processing and evaluation unit determining the capacitance and/or dielectric loss factor of a capacitor is known per se, there is no need for a detailed description thereof here. Evaluation can take place in analogue digital manner, e.g. with a micro-computer or a universal computer.

FIG. 1 merely shows the basic construction. A practical embodiment is shown in FIG. 2. In this embodiment, the two electrodes are "L"-shaped, and the leg of each "L" overlaps to enclose between them the membrane or diaphragm 3. An electrode support 6 fixes the position of electrodes 1 and 2 with respect to one another. At the end of the electrodes leads 5 are provided for the application of the a.c. voltage or the connection of the evaluation unit 10.

Hereinafter a description is provided of an embodiment for a sensor according to the invention for the purpose of measuring aqueous solutions and particularly the pH-value thereof and subsequently an embodiment more particularly suitable for the measurement of the alkalinity, viscosity and dispersant/detergent additive concentration in industrial oils.

pH-sensor

In the embodiment represented hereinafter, the two electrodes 1 and 2 are made from titanium and have a rutile or titanium aluminium zirconate coating 4. Coating 4 is not porous and is approximately 8 to 30 $\mu$m thick. Diaphragm 3 between the electrodes is approximately 10 to 100 $\mu$m thick and comprises non-porous corundum or gamma-aluminar. The sensor according to the invention when used as a pH-sensor can have the following dimensions:

Thickness 0.5 mm, width 5 mm and length 10 mm.

The frequency of the a.c. voltage applied by the signal processing and evaluation unit varies in a range between approximately 50 Hz and 1 GHz and preferably between 100 Hz and 40 KHz, while the peek voltage value is preferably approximately 1V.

If such a sensor is placed in the liquid to be measured, e.g. an aqueous solution, then ions diffuse into the diaphragm. The dielectric characteristics of the diaphragm 3 vary more particularly through the diffusing in of hydrogen and hydroxyl ions, so that the capacitance and dielectric loss factor are correlated with the pH-value. However, no ions diffuse into the non-porous coating 4 of electrodes 1 and 2, so that these electrodes continue to be insulated and the complex resistance of the sensor-capacitor is not modified by a galvanic bridging and this only takes place through the change to the dielectric characteristics of the diaphragm 3. As diaphragm 3 is not chemically attacked by the liquid, which only diffuses into the pores or into the actual material (e.g. mica), the reproducibility is high.

The evaluation unit stores the measured values in association with the particular measured frequency and compares these values with stored calibration data. From the comparison of the measured data and the stored calibration data, it is possible to very accurately and reproduceably determine the pH-values. As a result of the high reproducibility, it is possible to "precalibrate" the evaluation unit in such a way that it directly supplies the pH-value as a measurement result.

According to a particularly advantageous further development of the pH-sensor, which is particularly appropriate for use in medicine and biotechnology, a 5 to 20 $\mu$m thick ion-selective diaphragm capsule is placed round the sensor according to the invention and e.g. increases the selectivity for hydrogen and hydroxyl ions or potassium, sodium, chlorine or calcium ions. As a result of this selective interference, it is possible to determine these ions separately or separately from other interference charges.

oil sensor

The qualitative characteristics of engine oils and their mixtures, referred to hereinafter as oil for short, change through ageing on loading the oil. It is therefore necessary to replace the oils after a given period. As the "consumption" of the oil cannot be continuously monitored, the oil is often changed too early or in other cases remains too long in use, e.g. in a turbine, engine, vacuum pump or transformer.

Firstly an embodiment is described in which, as in the embodiments of FIGS. 1 and 2, the electrodes 1 and 2 are constructed in plate-like manner. The electrodes are e.g. made from pure titanium or a titanium alloy containing up to 6% aluminium, up to 4% vanadium and possibly traces of copper.

Electrodes 1 and 2 are once again provided with a non-conducting coating 4, which can be produced by anodic or glow oxidation of the electrode metal. In the illustrated embodiment on the titanium electrodes is formed a titanium (di) oxide coating with a thickness between approximately 8 and 20 $\mu$m by anodic oxidation in aqueous sodium sulphate solution. It is expressly pointed out that the characteristics of the titanium (di) oxide coating are dependent on the current density and the voltage during production. The process parameters during the production of coating 4 on the electrodes are consequently to be set in accordance with the desired coating characteristics.

The non-conducting porous diaphragm 3 preferably has a thickness between approximately 10 and 100 $\mu$m, the pore diameter being between 0.01 and 1.0 $\mu$m and preferably between 0.05 and 0.2 $\mu$m.

Such a diaphragm can e.g. be produced in that an aluminium foil with a thickness of 10 to 100 $\mu$m is completely oxidized in a 15% aqueous $H_2SO_4$ solution at constant current densities of approximately 10 mA/cm$^2$. The coating appropriately has pores with a specific surface of approximately 100 m$^2$/g.

A sensor with the aforementioned structure has e.g. the following typical dimensions:

Width 2 mm, length 25 mm and thickness 0.2 mm.

The electrodes can be rectangular, so that they form a "plate capacitor", but it is also possible to use cylindrical electrodes.

Typical dimensions of the cylindrical electrodes are diameter of the internal electrode 1 to 10 mm, which can be solid or in the form of a hollow cylinder with a wall thickness of e.g. 0.5 to 3 mm. The external electrode is a hollow cylinder with an internal diameter, which is the same as the external diameter of the internal electrode, plus the thickness of the porous coating of the internal electrode, its external diameter being between 2 and 15 mm. The length of the active part of the cylindrical electrode is approximately 1 to 5 mm.

In order to permit an easier oil passage to the porous intermediate coating, at least one of the two electrodes is advantageously made porous in such a way that also the inner walls of the pores are coated with metal oxide.

By means of an electronic evaluation unit, an a.c. voltage is applied to the electrodes and its frequency is variable between approximately 0.05 KHz and 1 GHz, while its peek voltage value is between approximately 1 and 5 V. On the basis of the behavior revealed by the sensor as a frequency-dependent, complex resistor, the evaluation unit determines a characteristic dielectric quantity of the sensor, in the embodiment the dielectric loss factor D, as a function of the measuring frequency f, $D=D(f)$. In the frequency-dependant course of the dielectric quantity, due to the aforementioned characteristic action of the porous, non-conducting diaphragm 3 of the sensor, there are very marked values and in the present case maxima of D, FIGS. 3, 5, and 7 showing maxima between 0.1 and 10 KHz. A maximum preceding these occurs under 0.1 KHz and is not covered by the drawings. Further maxima not covered by the drawings occur at values exceeding 40 KHz of measuring frequency f. The maxima of D include relaxation frequencies $f_r$ as a marked value of the measuring frequency f.

FIG. 3 shows the dependants of the dielectric loss factor as a function of the applied frequency in the case of new and used engine oil of type 15W40. It can be seen that the curve in the case of used oil is displaced towards higher dielectric loss factors for the same measuring frequencies, there being a maximum of D at $f_r$ of 1 KHz and it rises from $D=1.40$ to approximately $D=1.55$.

It is clear therefrom that during ageing, the average rise of the curve portions between the ordinate axis and the particular maximum of D has changed and as a tendency has become smaller. This is attributed to the fact that the aforementioned maximum, not shown in the drawing and occurring below 0.1 KHz is mainly due to the acidity of the oil and during ageing this has become larger than the alkalinity which is mainly expressed in the indicated maxima at approximately 1 KHz.

The ageing-dependant change to the average rise of $D=D(f)$ before reaching the relaxation frequency $f_R$ is evaluated according to the invention for determining the alkalinity and for at least two frequencies $f_1$ and $f_2$, the evaluation unit calculates the ratio $$A=(D(F_2)-D(f_1))/(f_2-f_1)$$

at a function course according to FIG. 2 to example $A=(D(400\ Hz)-D(100\ Hz))/300\ Hz$ and is indicated in each case as a measure of the instantaneous alkalinity. The value of the ratio A determined in this way can also be stored by the evaluation unit and compared with earlier values of A for indicating the alkalinity change.

FIG. 4 shows the development of $A=(D_{400}-D_{100})/\Delta f$. This value A=alkalinity decreases sharply with a falling pH-value and from this relationship it is possible to reliably determine the occurrence of acid groups in the alkaline oil.

FIG. 5 gives measured values of $D=D(f)$ with oils having viscosities of $n=1.3$ and 79 cP. With rising values of n, The relaxation frequencies of the D-maxima are displaced from approximately 1.3 KHz to approximately 150 Hz. This phenomenon called maximum displacement can be used for determining the viscosity $\Sigma$ of an oil.

In general the relative increase of the maximum frequencies $\Delta f/f$ is a measure for the relative decrease in the viscosity $-\Delta n/n$.

In per se known, conventional manner this relationship can be provided with a calibration factor and used for evaluating oil characteristics, preferably using a computer.

FIG. 6 shows the connection between the viscosity and relaxation time t, the represented quantity $k_n=t\ 10^3$ and $t=\frac{1}{2}\pi f$. The curve is recorded with constant alkalinity.

FIGS. 5 and 6 relate to the maximum occurring during $D=D(f)$, the rising lines being associatable with a specific D-maximum. For several maxima, there is a bunch of corresponding lines starting at the origin with different slopes. As the position of the maxima is also influenced by the conductivity and consequently the alkalinity of the oil it is advantageous to eliminate this influence in that account is taken of several maxima and the maximum displacement are determined with more than 2 to 4 frequencies (f).

In the case of a simultaneous large change of alkalinity, it is recommended that account be taken of the relative alkalinity change $Db/b$ in accordance with the diagram $$\frac{\Delta n}{n} = \frac{-\Delta f}{f}k_1 + \frac{\Delta b}{b}k_2$$

k being calibrated in at calibration factors.

For determining the change of the concentration of the additives of the oil, according to the invention the dependence of the concentration on the value of a specific maximum of D is recorded, preferably by adding particular additives to the oil and storing in the evaluation unit. The change to the instantaneous value of this maximum determined by the evaluation unit compared with the initial value thereof can be used as a measure for the concentration change.

FIG. 7 shows a displacement of the maximum from $D=2.0$ to $D=2.3$ on an additive concentration decrease from 10 to 3.3%.

The invention has been described in exemplified manner hereinbefore, various modifications being possible within the general inventive concept, e.g. it being possible to use several sensors, so as to be able to determine separately the individual oil properties.

We claim:

1. A sensor for detecting the ageing of oil comprising electrodes (1, 2) having an electrically insulating and essentially oil-tight coating, positioned between said electrodes, a non-conducting diaphragm (3) which is made of an oil-tight material which has continuous pores which penetrate through the diaphragm and into which the oil to be tested can penetrate, and an evaluation unit attached to said electrodes, which determines the dielectric loss factor and/or the capacity of the electrodes at one or more frequencies.

2. Sensor according to claim 1, characterized in that the electrodes (1, 2) essentially are formed of a material selected from the group consisting of aluminum, zirconium, titanium, tantalum, tungsten and molybdenum.

3. Sensor according to claim 1 characterized in that the non-conducting diaphragm (3) essentially is formed of a material selected from the group consisting of alumina, silicon nitride, $KAl_2(OH)_2 \cdot AlSi_3O_{10}$ and polytetrafluoroethylene.

4. Sensor according to claim 1, characterized in that the electrically insulating coatings (4) of electrodes (1, 2) essentially is formed of a material selected from the group consisting of non-conducting metal oxide, mixed metal oxide and metal nitride.

5. Sensor according to claim 4, characterized in that the coating is produced by direct oxidation of the electrode material to a material selected from the group consisting of zirconium oxide, titanium oxide, tantalum oxide, tungsten oxide, molybdenum oxide and aluminum oxide.

6. Apparatus according to claim 4, characterized in that the coating is produced by either direct oxidation or by glow oxidation.

7. Sensor according to claim 1, characterized in that the coatings (4) are formed of a material selected from the group consisting of amphoteric oxides and mixed oxides.

8. Sensor according to claim 1, characterized in that the coating thickness is between 5 and 30 μm.

9. Sensor according to claim 1, characterized in that the electrodes (1, 2) are formed of a material selected from the group consisting of pure titanium and titanium alloys, while the electrode coatings (4) are of $TiO_2$ and the diaphragm (3) of $Al_2O_3$.

10. Sensor according to claim 1, characterized in that the coatings (4) and diaphragm (3) essentially comprise the same basic chemical material, optionally with different structures.

11. Sensor according to claim 1, characterized in that the non-conducting diaphragm (3) is porous with through pores, the pore diameter being between approximately 0.01 and 1 μm preferably 0.05 to 0.2 μm.

12. Sensor according to claim 1, characterized in that at least one electrode (1 or 2) is porous and has an inner and an outer wall, and the porous inner wall of the electrode has a non-conducting, liquid-tight coating (4).

13. Sensor according to claim 1, characterized in that the diaphragm thickness is 10 to 100 μm, preferably 20 to 40 μm.

14. Sensor according to claim 1, characterized in that the non-conducting diaphragm (3) comprises a material with a layer structure, which can be penetrated by the liquid to be investigated.

15. Sensor according to claim 14, characterized in that the diaphragm is formed of a material selected from the group consisting of non-porous corundum, aluminum hydroxyl silicate and gamma-alumina.

16. Sensor according to claim 15, characterized in that the diaphragm thickness is between approximately 6 and 100 μm, preferably 30 and 40 μm.

17. Sensor according to claim 1, characterized in that the electrodes face one another in the manner of a plate capacitor.

18. Sensor according to claim 1, characterized in that one electrode (1) cylindrically surrounds the other electrode (2), the diaphragm surrounding the inner electrode.

19. Apparatus for measuring the characteristics of a liquid with a sensor according to claim 1 and which is immersed in the liquid to be investigated characterized in that a signal processing and evaluation unit applies an a.c. voltage to both electrodes (1, 2), the a.c. voltage frequency varies between 50 hz and 1 GHz and the dielectric loss factor $D = D(f)$ and/or the capacitance $C = C(f)$ being measured at different frequencies and that the evaluation unit compares the measured values $D(f)$ and $C(f)$ with stored reference values $D_{ref}(f)$ or $C_{ref}(f)$.

20. Apparatus according to claim 19, characterized in that for determining the alkalinity, particularly of an oil, the evaluation unit calculates the value A in accordance with the relationship $$A = (D(f_2) - D(f_1))/(f_2 - f_1),$$

in which $D(f_1)$ is the dielectric loss factor at the frequency $f_1$ and compares the measured value A with a stored reference value $A_{ref}$ and supplies the variation or the measured and optionally corrected value A directly as a measure for the alkalinity.

21. Apparatus according to claim 20, characterized in that on exceeding a predetermined limit value of either $D(f_r)$, $C(f_r)$, or data calculated therefrom, the evaluation unit supplies a signal for a control quantity.

22. Apparatus according to claim 19, characterized in that the evaluation unit determines one or more maxima of the dielectric loss factor $d(f)$ as a function of the frequency of the applied a.c. voltage for determining the viscosity of liquid and from the comparison of the frequencies with reference frequencies at which maxima occur in a reference liquid, the viscosity of the investigated liquid is determined.

23. Apparatus according to claim 22, characterized in that the evaluation unit determines an additive concentration from the level of the maxima.

24. Apparatus according to claim 19, characterized in that the evaluation unit compares the measured capacitance/frequency value pairs with stored capacitance/frequency value pairs and associates a pH-value with the value pairs.

25. Apparatus according to claim 1, characterized in that the evaluation unit compares the measured dielectric loss factor/frequency value pairs with stored dielectric loss factor/frequency value pairs.

* * * * *

UNITED STATES PATENT AND TRADEMARK OFFICE
CERTIFICATE OF CORRECTION

PATENT NO. : 5,269,175

DATED : Dec. 14, 1993

INVENTOR(S) : Horst Chmiel; Gunter Hellwig; and Herbert Bauser

It is certified that error appears in the above-identified patent and that said Letters Patent is hereby corrected as shown below:

Column 12, line 37, delete "d" and insert therefor -- D --.

Signed and Sealed this

Thirteenth Day of September, 1994

Attest:

Attesting Officer

BRUCE LEHMAN

Commissioner of Patents and Trademarks